(12) United States Patent
Maracaja et al.

(10) Patent No.: US 11,679,247 B2
(45) Date of Patent: Jun. 20, 2023

(54) APPARATUS FOR PROTECTING PERCUTANEOUS CONNECTIONS AND RELATED METHODS

(71) Applicants: Luiz Maracaja, San Antonio, TX (US); Edward Sako, San Antonio, TX (US)

(72) Inventors: Luiz Maracaja, San Antonio, TX (US); Edward Sako, San Antonio, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 319 days.

(21) Appl. No.: 16/763,797

(22) PCT Filed: Nov. 13, 2018

(86) PCT No.: PCT/US2018/060637
§ 371 (c)(1),
(2) Date: May 13, 2020

(87) PCT Pub. No.: WO2019/094890
PCT Pub. Date: May 16, 2019

(65) Prior Publication Data
US 2020/0353237 A1    Nov. 12, 2020

Related U.S. Application Data

(60) Provisional application No. 62/654,331, filed on Apr. 7, 2018, provisional application No. 62/621,209, filed on Jan. 24, 2018, provisional application No. 62/593,729, filed on Dec. 1, 2017, provisional application No. 62/584,987, filed on Nov. 13, 2017, (Continued)

(51) Int. Cl.
*A61M 39/22* (2006.01)
*A61L 2/10* (2006.01)
*A61L 2/26* (2006.01)
*A61M 39/16* (2006.01)

(52) U.S. Cl.
CPC ............ *A61M 39/223* (2013.01); *A61L 2/10* (2013.01); *A61L 2/26* (2013.01); *A61M 39/165* (2013.01); *A61L 2202/11* (2013.01); *A61L 2202/122* (2013.01); *A61L 2202/123* (2013.01); *A61L 2202/24* (2013.01); *A61M 2039/229* (2013.01); *A61M 2205/3306* (2013.01); *A61M 2205/52* (2013.01)

(58) Field of Classification Search
CPC .......... A61L 2/10; A61L 2/26; A61M 39/223; A61M 39/165
See application file for complete search history.

(56) References Cited

U.S. PATENT DOCUMENTS

| 3,437,803 A | 4/1969 | Seitz et al. |
| 3,490,736 A | 1/1970 | Snyder |

(Continued)

FOREIGN PATENT DOCUMENTS

| WO | WO 2002/102421 | 12/2002 |
| WO | WO 2011/127043 | 10/2011 |
| WO | WO 2019/164988 | 8/2019 |

OTHER PUBLICATIONS

International Search Report and Written Opinion issued in corresponding International Patent Application No. PCT/US2018/060637 dated Jan. 16, 2019, 13 pages.

*Primary Examiner* — Sean E Conley

(57) ABSTRACT

Certain aspects are directed to a housing and cap to provide protection of medical devices having one or more percutaneous connection (e.g., a three-way stopcock or catheter port).

20 Claims, 13 Drawing Sheets

Related U.S. Application Data provisional application No. 62/585,480, filed on Nov. 13, 2017.

(56) References Cited

U.S. PATENT DOCUMENTS

| | | |
|---|---|---|
| 4,538,434 A | 9/1985 | Janzen et al. |
| 5,203,351 A | 4/1993 | Adell |
| 6,099,735 A | 8/2000 | Kelada |
| 6,457,488 B2 | 10/2002 | Loo |
| RE38,145 E | 6/2003 | Lynn |
| 7,043,060 B2 | 5/2006 | Quintana |
| 8,603,022 B2 | 12/2013 | Lyons et al. |

APPARATUS FOR PROTECTING PERCUTANEOUS CONNECTIONS AND RELATED METHODS

CROSS-REFERENCE TO RELATED APPLICATIONS

This application is a national phase under 35 U.S.C. § 371 of International Application No. PCT/US2018/060637, filed Nov. 13, 2018, which claims the benefit of priority to U.S. Provisional Patents Ser. No. 62/584,987 filed Nov. 13, 2017; 62/585,480 filed Nov. 13, 2017; 62/593,729 filed Dec. 1, 2017; 62/621,209 filed Jan. 24, 2018; and 62/654,331 filed Apr. 7, 2018, each of which are incorporated herein by reference in their entirety.

BACKGROUND

This application relates to apparatuses, systems, and methods for protecting percutaneous connections.

A common example of a percutaneous connection is the three-way stopcock. The three-way stopcock is a valve or turning plug that controls the flow of fluid from a container through a tube (see FIGS. 1A and 1B). The three-way stopcock has an inlet, an outlet, and a side port. A three-way stopcock can be used in conjunction with intravenous (IV) tubing to stop or start flow of a solution, or stop flow of a first solution and allow the flow of a second solution. It provides 3-way flow (from inlet to outlet, inlet to side-port, or side port to outlet) by use of the handle on the top of the stopcock to open and close lines. The three-way stopcock can also be used to reduce the number of IV lines down to one, for easier administration of drugs/drug infusion purposes. Three-way stopcocks are convenient for medication administration, blood draw, and pressure transducing. They are part of every venous line, arterial line, or other therapy assembly tubing system used in current clinical practice.

The use of three-way valve systems is associated with problems such as bacterial contamination, accidental medication injection, poor position, and pressure related skin lesions. Accidental intra-arterial or central nervous system injection of medication can cause severe complications. The standard diameter of conventional syringes, injection ports, and three-way stopcock systems is the same for venous, arterial, pulmonary artery, and other catheters. As such, health care providers can easily select the wrong port, leading to an error in medication administration.

Bacterial contamination of stopcocks is a serious problem in intensive care units. The contamination ultimately will cause central line associated blood stream infection (CLABSI), which is a serious infection that occurs when microbes (usually bacteria or viruses) enter the bloodstream through the central line. Healthcare providers must follow a strict protocol when inserting the line to make sure the line remains sterile and CLABSI does not occur. In addition to inserting the central line properly, healthcare providers must also use stringent infection control practices when accessing the central line. Removing a cap of the open stopcock opens a direct port to the IV line and is subject to touching non-sterile surfaces. This results in contamination. Needleless systems do not provide adequate protection from contamination. The best way to prevent contamination is to cap the stopcock. In practice, the manipulation of the stopcock and cap is almost always performed without sterile gloves which increases the risk of contamination. The use of sterile gloves in not economically viable for all IV and stopcock manipulations as well as IV administrations. Thus there remains a need for a device to minimize the contamination risk during the use of a percutaneous connector (e.g., a multiport stopcock).

SUMMARY

This application relates to apparatuses, systems, and methods for protecting, germ sterilization, and function tracking percutaneous connections or surgically placed drainage systems. The herein apparatus aim to protect patients from medication administration errors. Certain aspects are directed to a housing and cap to provide protection of medical devices having one or more percutaneous connection (e.g., a three-way stopcock or catheter port). Such devices may include one or more of the following features.

Certain embodiments are directed to, but not limited to, a housing having two sides, each side having a top forming an external surface and a bottom forming an internal surface, and each side configured so that the bottom edges of each side are adjacent or contact each other when the housing is closed. In certain aspects a side can include 1, 2, 3, 4, 5, 6, or more parts incorporating one or more feature described herein. The sides may be connected by a hinge such that the sides can be opened and closed. In one configuration the sides can be snapped or locked in place when the device is closed. The snap or locking mechanism can be reversible so that the device can be locked and unlocked at will. In certain aspects the snap or lock may be opposite the hinge. The two sides, when in the closed position, form a chamber configured to wrap around or enclose a medical device with one or more percutaneous connections (e.g., a three-way stopcock or catheter port). In certain aspects the opening and closing of the housing may be performed manually. In certain aspects the hinge need not be aligned with the snaps and locking mechanisms and can be positioned at various positions along the circumference of the device.

A housing as described and depicted herein can prevent the three-way stopcock from turning or being accidentally moved to an unfavorable position. The internal surface of the device can have locking bars that position or stabilize portions of the stopcock or medical device with a percutaneous connector. When the housing is closed, the bars are positioned on one or both sides of the turning selection knob or handle of the stopcock mechanism so that the knob or handle cannot be opened or closed accidentally, i.e., the device locks the stopcock in a selected position.

In certain embodiments the external surface of one or both sides can have a label. The label can be adhered to, imprinted into, engraved in or otherwise visible on the external surface of the device. In one aspect the label will identify the specific purpose of a percutaneous connection to which the device is affixed, e.g., the word "arterial" to indicate that particular multiport or stopcock provides access to arterial blood flow or the arterial system of a subject. The labeling feature can help prevent accidental administration of medications and other misidentification problems. Besides words the external surface may have other signs and symbols to alert the provider, e.g., forbidden sign or symbol for medication injection. The labeling feature can help prevent accidental administration of medications and other misidentification problems. In certain aspects the label can read arterial, venous, or some other informational indicator. In a particular aspect the housing when closed minimizes sharp or rough edges to minimize rub injury to a subject's skin.

In other examples, the housing can be configured to prevent or mitigate contamination of a medical device with a percutaneous connection. In certain aspects the housing is configured to prevent bacterial contamination and to provide or provide for UV light sterilization. The device can have a cap located along and attached, in certain aspects moveably attached to the inner surface of one side or the other, or attached to the hinge region of the housing. An internal or external UV light source can be configured to illuminate the medical device with a percutaneous connection and/or connections or caps. The UV light can be an LED. The UV light can be an LED or other lamp or bulbs with emission of UV light with appropriate frequency for germ sterilization. The UV source can be connected to a battery, control chip, and circuits needed for its operation. Ultraviolet germicidal irradiation (UVGI) is a disinfection method that uses short-wavelength ultraviolet light to kill or inactivate microorganisms by destroying nucleic acids and disrupting their DNA, leaving them unable to perform vital cellular functions. The application of UVGI to disinfection has been an accepted practice since the mid-20th century. It has been used primarily in medical sanitation and sterile work facilities. UV radiation used in most germicidal bulbs is harmful to both skin and eyes, and should not be used in any fixture or application that was not designed specifically to prevent exposure to humans or animals. Chronic effects include accelerated skin aging and skin cancer. The device described herein provides UV light germicidal radiation inside the housing and prevents any external exposure or contact with outside environment. UV light sterilization can be contained inside of the device. In certain aspects the UV light therapy is initiated with the locking of the device and interrupted with opening of the device.

Other embodiments are directed to valve connectors (e.g., three way stopcock) made of materials with high transmittance to ultraviolet-C light such as quartz or quartz-like materials such as or; fused silica (e.g., INFRASIL™, SUPRASIL™, OPTOSIL™, and the like); borosilicate glass; magnesium fluoride; calcium fluoride; lithium fluoride; zinc selenide; sapphire; borosilicate glass; light transmitting polymers such as polydimethylsiloxane (PDMS), polyvinyldiene fluoride, 1H,1H,2H,2H-Perfluorodecyl methacrylate; 1H,1H,2H,2H-Nonafluorohexyl-1-methacrylate; 1H,1H,2H,2H-Tridecafluorooctyl-1-methacrylate; 1H,1H,2H,2H-Tridecafluorooctyl acrylate; 2-Perfluorobutylethyl acrylate, 2,2,3,4,4,4-Hexafluorobutyl methacrylate and copolymers comprising the same; silicon, teflon and other. These valve connectors can be used in conjunction with the housings described in this disclosure. Based on microbiologic studies the inventor found the plastic polymer with low transmittance on the connector hub works as a protector shield germs from antimicrobial light exposure. Therefore, there is a need for a hub, cap or the entire three-way to be made of materials with high UV-C transmittance to allow exposure of the stopcock to antimicrobial treatments.

In a clinical setting the cap that covers the stopcock is very small and is frequently lost or forgotten. Thus the stopcock is frequently left without a cover and exposed, increasing the risk of contamination. A cap integrated into the housing prevents it from getting lost since it is attached to the housing, i.e., the line guard device. Alternatively, the cap can be attached to a thread or tether attached to the housing. In certain aspects the cap integrated with the housing is made of borosilicate glass or a polymer that transmits UV light. The UV light can be turned on or pulsed periodically or at will to sterilize the stopcock positioned inside the housing. The reflective internal surface of the housing can allow for distribution of the UV radiation throughout the chamber formed by the housing providing sterilization of the stopcock or medical device with a percutaneous connection contained within the housing, thus, preventing or inhibiting bacterial growth. The housing can include a UV transmittance window to allow a light source external to the housing to illuminate the medical device with a percutaneous connection inside the housing. The electronic components of the housing can be located inside the housing or alternatively outside of the housing with addition of a window for the UV light source. In certain aspects housing can be design as a disposable housing that can be used in conjunction with a non-disposable UV source component. The UV source component can be connected to a power outlet or a battery.

The shape of the housing can be modified to provide UV light therapy to different parts of indwelling catheters, drains, drive lines for ventricular assist devices and other devices with percutaneous connections.

In certain aspects the device can be equipped with non-UV light to illuminate the device. During night certain medications need to be administered on scheduled basis. In order for a medical professional to find the three way stopcock they frequently have to turn the on the room lights and disturb the patients who are sleeping. This is an serious problem in that sleep is a very important for recovery of a sick patient. Sleep deprivation can cause serious problems such as memory loss, cognitive dysfunction, disorientation, and delirium. The line guard can have a non-UV light LED allowing the medical professional to easily find the stopcock without having to turn room lights on. Once the device is located, which also includes location of the medication port. In certain aspects, once the device is located and open the medication port remains illuminated so the lights can remain off during medication administration. Upon opening the shell one would have full visualization of the injection port. Using the nigh illumination aspect allows medication to be administered without disturbing patient sleep.

In certain aspects the device can be disposable and be attached to non-disposable multifunction unit. Functions such as one or more of event-time registration, memory storage, timer activation, non-led light color coding, optic sensor for detection of biofilm, fingerprint reader, mini-camera and mini-speaker. A non-disposable attachment adds features with external computer connectivity.

Certain embodiments are directed to a housing assembly (e.g., Line Guard™) that includes a first housing body; a second housing body pivotally coupled to the first housing body, first and second housing body being moveable relative to each between an open and closed position, wherein the housing assembly forms an interior chamber with one or more openings when in the closed position; a cap configured to be disposed within the interior chamber and configured to receive a complementary. The housing can further include a locking mechanism within the interior chamber in locking engagement when the housing assembly is in the closed position and unlocked when the housing assembly is in the open position. In certain aspects chamber has a reflective surface. The housing can further include a mateable latch having (a) a lip region on the first housing body; and (b) a lip-receiving region on the second housing body. The housing assembly may also further include a hinge pivotally connecting the first housing body and the second housing body to allow rotation of the first housing body and second housing body between an open position and a closed position. In certain aspects the first housing body and second housing body can have a smooth outer surface. In still a further aspect the housing assembly can have a light transmittable region in the first housing body or second housing body, or the first housing body and the second housing body. The housing assembly can have a cap integrally formed with or connected to the hinge. In still a further aspect the housing assembly can have a cap that is operatively coupled to a light source. The cap can be made of borosilicate glass or a UV light transmittable polymer. In certain aspects the cap is made of a light transmittable polymer. The light source can be an external light source or an integrated light source. The external light source can be a pulsed xenon, LED, mercury lamp, or other source of UV-C radiation that is provided through the window of the housing at a scheduled time, on demand, or after manipulation of the percutaneous connection (e.g., a three-way stopcock).

Certain embodiments are directed to a housing assembly having a first housing body; a second housing body pivotally coupled to the first housing body, first and second housing body being moveable relative to each between an open and closed position, wherein the housing assembly forms an interior chamber with one or more openings when in the closed position; a locking mechanism within the interior chamber configured to immobilize a portion of a percutaneous device when the housing assembly is in the closed position. The housing assembly can further include a cap disposed within the interior chamber and configured to receive a port or a medical device connector. The interior chamber can have one or more reflective surface. The housing assembly can further include a mateable latch having (a) a lip region on the first housing body; and (b) a lip-receiving region on the second housing body. The housing assembly can also further include a hinge pivotally connecting the first housing body and the second housing body to allow rotation of the first housing body and second housing body between an open position and a closed position. The first housing body and second housing body can have a smooth outer surface. The housing assembly can include a light transmittable region in the first housing body or second housing body, or the first housing body and the second housing body. The cap can be integrally formed with the hinge or otherwise connected. The cap can be operatively coupled to a light source. In certain aspects the cap is made of borosilicate glass a light transmittable polymer. The light source can be an external light source or incorporated into the housing.

In certain embodiments the device is disposable and the UV light source component is attachable to the disposable portion but is not itself disposable and can be reused. The non-disposable portion can include integrated computer chip(s) and electronic circuits that provide additional functionality such as event-time registration, memory storage, timer activation, non-led light color coding, optic sensor for detection of biofilm, fingerprint reader, mini-camera and mini-speaker. Non-disposable attachment adds features with external computer connectivity. This feature allows tracking between the medication orders and the actual time when the line guard was open for medication administration. Upon connection with computer and respective custom software, different data such as events, time logs, intervals, battery life and others can be correlated with medication orders. In certain aspects non UV light LED color coding and mini-speaker are used for battery life status and for deliver message upon opening or closing the halves of the line-guard.

Certain embodiments are directed to methods of using a device described herein by connecting a cap of an open housing assembly port or a connector present on a medical device; rotating the first housing body relative to the second housing body from the open position to the closed position; engaging the mateable latch to enclose a portion of medical the device within the interior chamber; and optionally activating a light source to sanitize the port and/or connector.

Certain aspects can be directed to an apparatus having 1, 2, 3, 4, 5, or more features selected from (i) physical protection for three-way stopcock or shell, (ii) locking bars, (iii) labeling system, (iv) night light illumination, and/or (v) UV-C germicidal capabilities.

Other embodiments of the invention are discussed throughout this application. Any embodiment discussed with respect to one aspect of the invention applies to other aspects of the invention as well and vice versa. Each embodiment described herein is understood to be embodiments of the invention that are applicable to all aspects of the invention. It is contemplated that any embodiment discussed herein can be implemented with respect to any method or composition of the invention, and vice versa. Furthermore, compositions and kits of the invention can be used to achieve the methods described herein.

The use of the word "a" or "an" when used in conjunction with the term "comprising" in the claims and/or the specification may mean "one," but it is also consistent with the meaning of "one or more," "at least one," and "one or more than one."

Throughout this application, the term "about" is used to indicate that a value includes the standard deviation of error for the device or method being employed to determine the value.

The use of the term "or" in the claims is used to mean "and/or" unless explicitly indicated to refer to alternatives only or the alternatives are mutually exclusive, although the disclosure supports a definition that refers to only alternatives and "and/or."

The term "coupled" is defined as connected, although not necessarily directly, and not necessarily mechanically; two items that are "coupled" may be unitary with each other.

The terms "a" and "an" are defined as one or more unless this disclosure explicitly requires otherwise.

The term "substantially" is defined as largely but not necessarily wholly what is specified (and includes what is specified; e.g., substantially 90 degrees includes 90 degrees and substantially parallel includes parallel), as understood by a person of ordinary skill in the art. In any disclosed embodiment, the term "substantially" be substituted with "within [a percentage] of" what is specified, where the percentage includes 0.1, 1, or 5 percent; and the term "approximately" may be substituted with "within 10 percent of" what is specified.

The phrase "and/or" means and, or. To illustrate, A, B, and/or C includes: A alone, B alone, C alone, a combination of A and B, a combination of A and C, a combination of B and C, or a combination of A, B, and C. In other words, "and/or" operates as an inclusive or.

Further, a device or system that is configured in a certain way is configured in at least that way, but it can also be configured in other ways than those specifically described.

The terms "comprise" (and any form of comprise, such as "comprises" and "comprising"), "have" (and any form of have, such as "has" and "having"), and "include" (and any form of include, such as "includes" and "including"). As a result, an apparatus that "comprises," "has," or "includes" one or more elements possesses those one or more elements, but is not limited to possessing only those one or more elements. Likewise, a method that "comprises," "has," or "includes" one or more steps possesses those one or more steps, but is not limited to possessing only those one or more steps.

Any embodiment of any of the systems, methods, and article of manufacture can consist of or consist essentially of—rather than comprise/have/include—any of the described steps, elements, and/or features. Thus, in any of the claims, the term "consisting of" or "consisting essentially of" can be substituted for any of the open-ended linking verbs recited above, in order to change the scope of a given claim from what it would otherwise be using the open-ended linking verb.

The feature or features of one embodiment may be applied to other embodiments, even though not described or illustrated, unless expressly prohibited by this disclosure or the nature of the embodiments.

Some details associated with the embodiments are described above, and others are described below.

DESCRIPTION OF THE DRAWINGS

The following drawings form part of the present specification and are included to further demonstrate certain aspects of the present invention. The invention may be better understood by reference to one or more of these drawings in combination with the detailed description of the specification embodiments presented herein.

DETAILED DESCRIPTION OF ILLUSTRATIVE EMBODIMENTS

The following discussion is directed to various embodiments of the invention. The term "invention" is not intended to refer to any particular embodiment or otherwise limit the scope of the disclosure. Although one or more of these embodiments may be preferred, the embodiments disclosed should not be interpreted, or otherwise used, as limiting the scope of the disclosure, including the claims. In addition, one skilled in the art will understand that the following description has broad application, and the discussion of any embodiment is meant only to be exemplary of that embodiment, and not intended to intimate that the scope of the disclosure, including the claims, is limited to that embodiment.

I. System Embodiment

Figure 2:
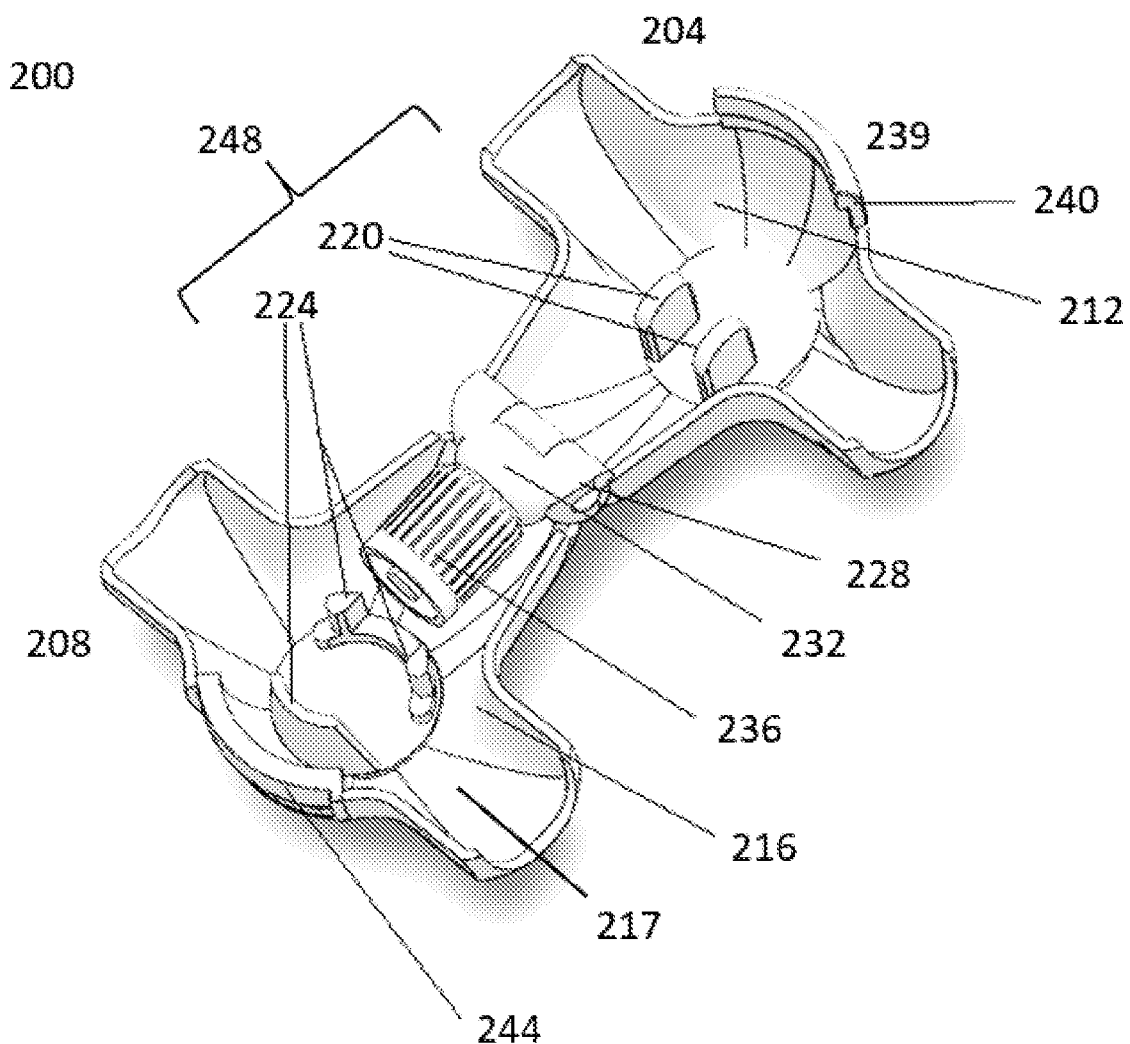
FIG. 2 is a perspective view of a representative housing in an open configuration.
Figure 3:
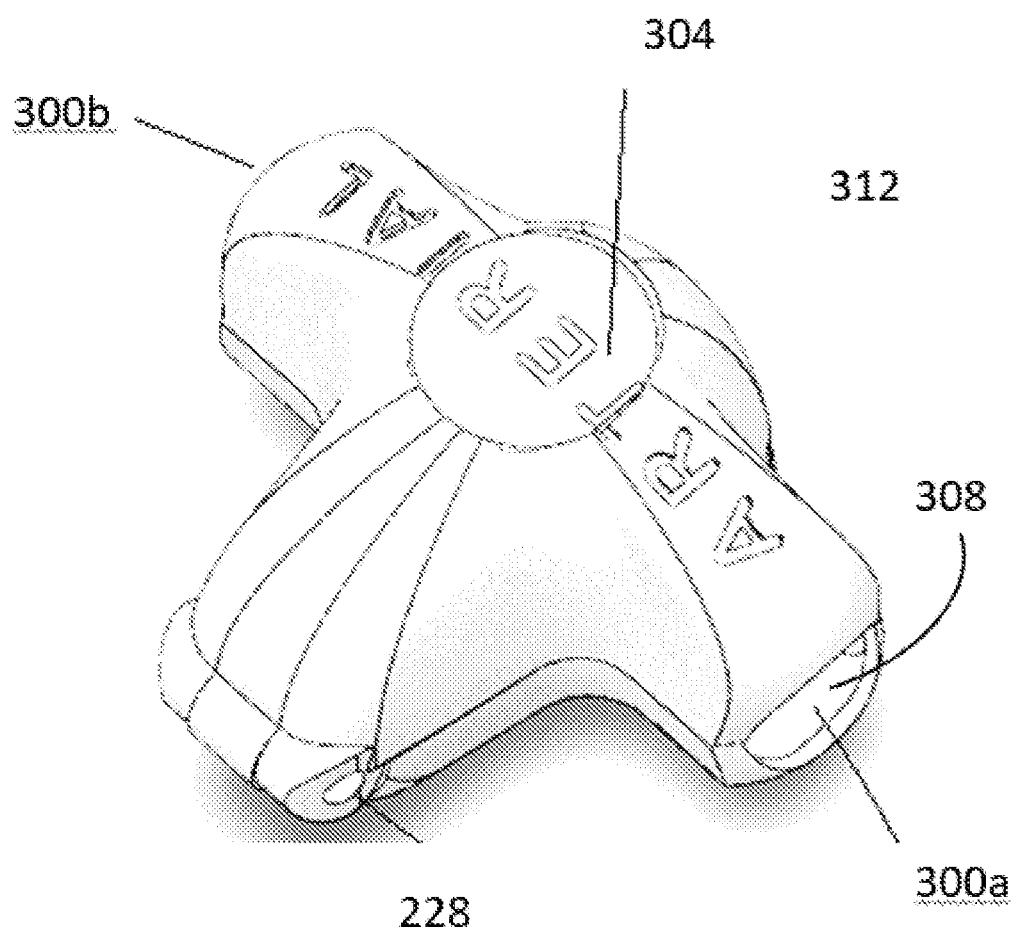
FIG. 3 is a perspective view of a representative housing in a closed configuration.
Figure 4:
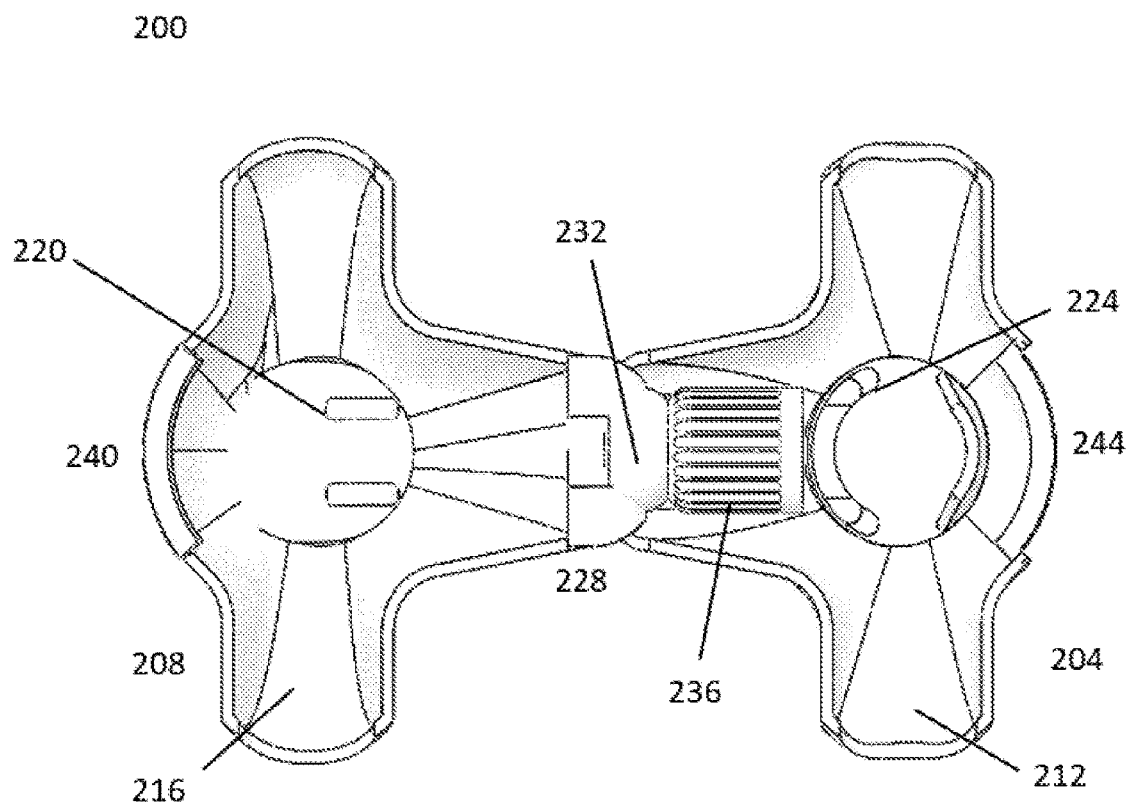
FIG. 4 is a top view of a representative housing in an open configuration.

Referring to FIG. 2 and FIG. 3, the housing assembly 200 includes a first housing body 204 coupled to a second housing body 208, where the first and second housing body 204, 208, are moveable relative to each between an open position 248 and closed position 312. The housing assembly 200 forms an interior chamber 308 with one or more openings 300a, 300b, when in the closed position 312. Housing assembly 200 also includes one or more cap 236 disposed within the interior chamber 308. Cap 236 may be configured to receive a percutaneous connection on a medical device (e.g., female luer on a three-way stopcock). The interior chamber 308 may have a reflective surface 217. The housing assembly 200 can also include a mateable latch 239 having a lip region 240 on the first housing body 204, and a lip-receiving region 244 on the second housing body 208. Hinge 228 may pivotally connect the first housing body 204 and the second housing body 208 to allow rotation of the first housing body 204 and second housing body 208 between the open position 248 and closed position 312.

Figure 5:
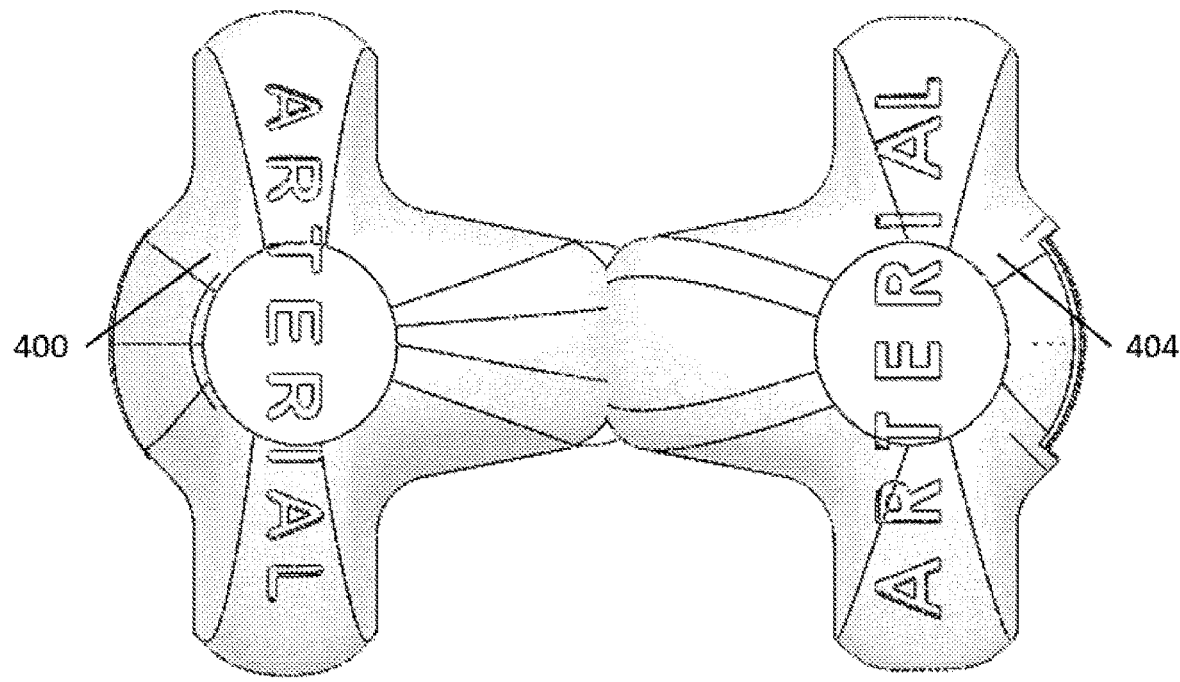
FIG. 5 is a bottom view of a representative housing in an open configuration.
Figure 6:
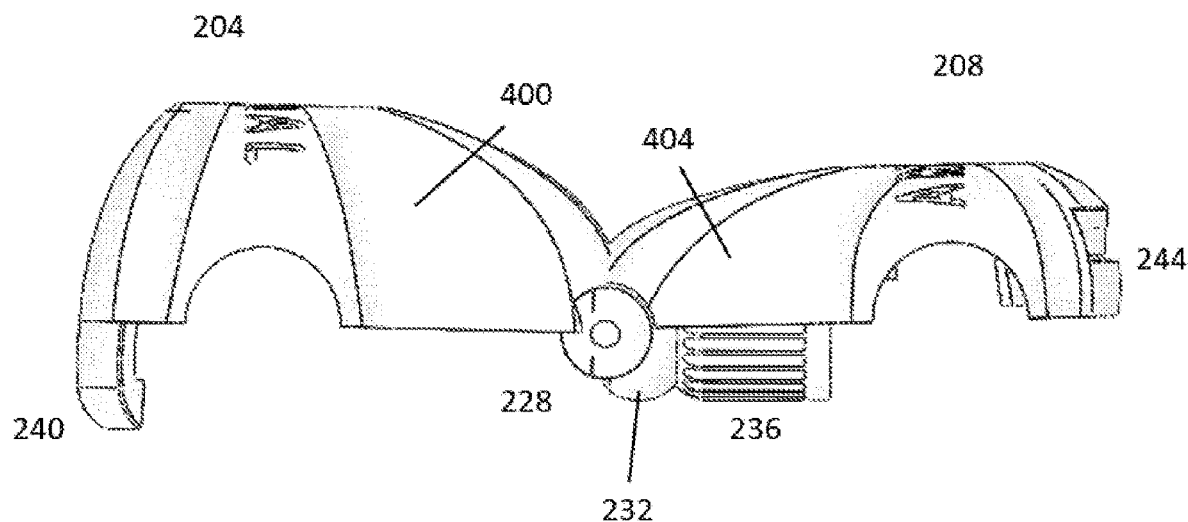
FIG. 6 is a first side view of a representative housing in an open configuration.
Figure 7:
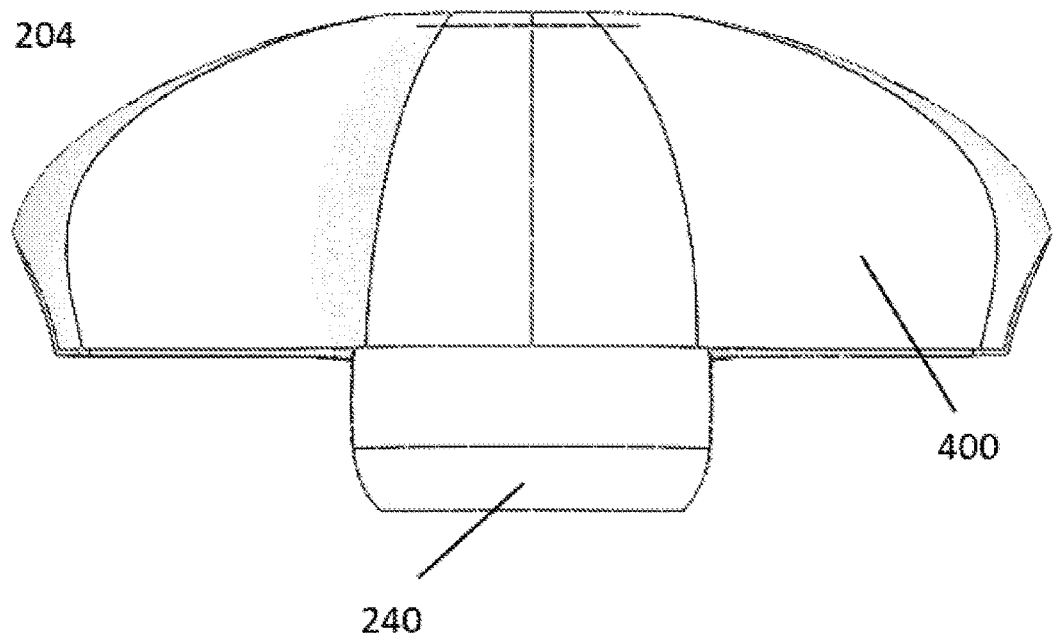
FIG. 7 is a front view of a representative housing in an open configuration.
Figure 8:
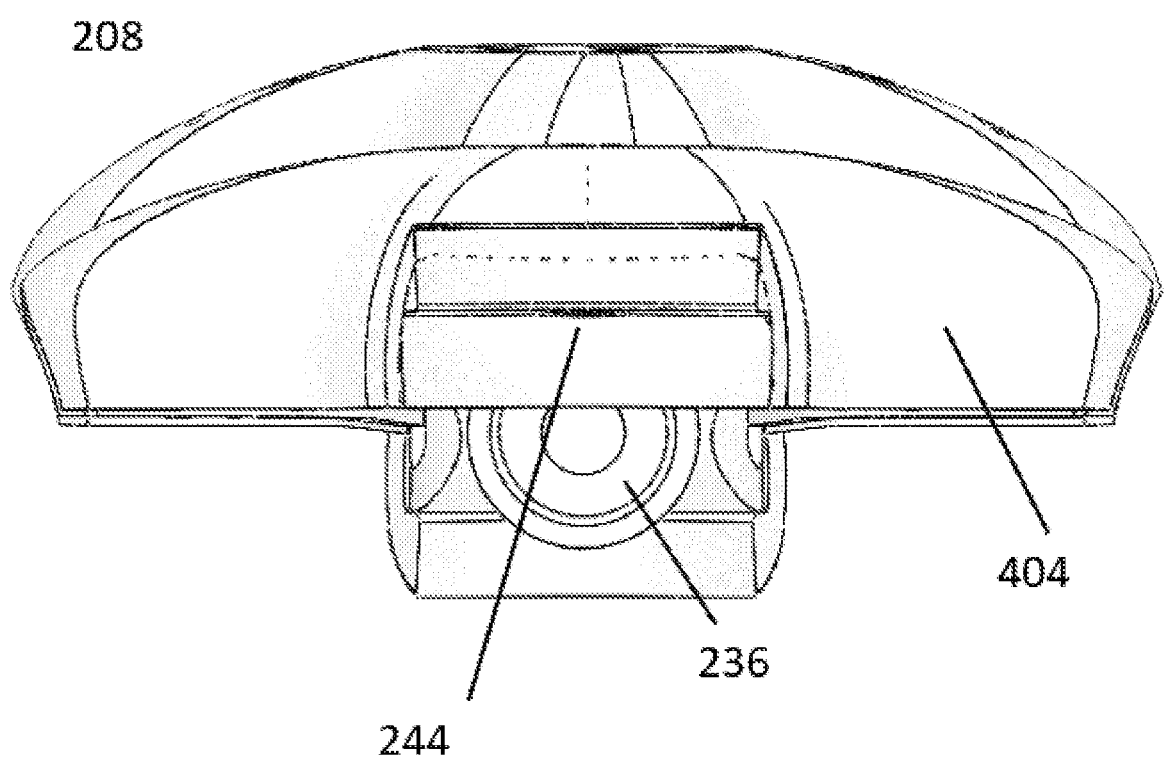
FIG. 8 is a back view of a representative housing in an open configuration.

Referring to FIG. 5, the first housing body 204 and second housing body 208 may have a smooth outer surface defined by a first housing body outer surface 400 and second housing body outer surface 404. Label 304 can be adhered to, imprinted into, engraved in, or otherwise visible on an outer surface of the housing assembly 200.

In a particular embodiment, housing assembly 200 includes a locking mechanism male end 220 disposed on first housing body inner surface 212 and a locking mechanism female end 224 disposed on second housing body inner surface 216. Locking mechanism male end and female end 220, 224, are in locking engagement when housing assembly 200 is in closed position 312 and unlocked when housing assembly 200 is in open position 248. Cap 236 may be made of borosilicate glass or other light transmittable materials and include a light source 232 disposed within the cap 236 that may be used to sanitize a percutaneous connection when connected to the cap 236.

Figure 9:
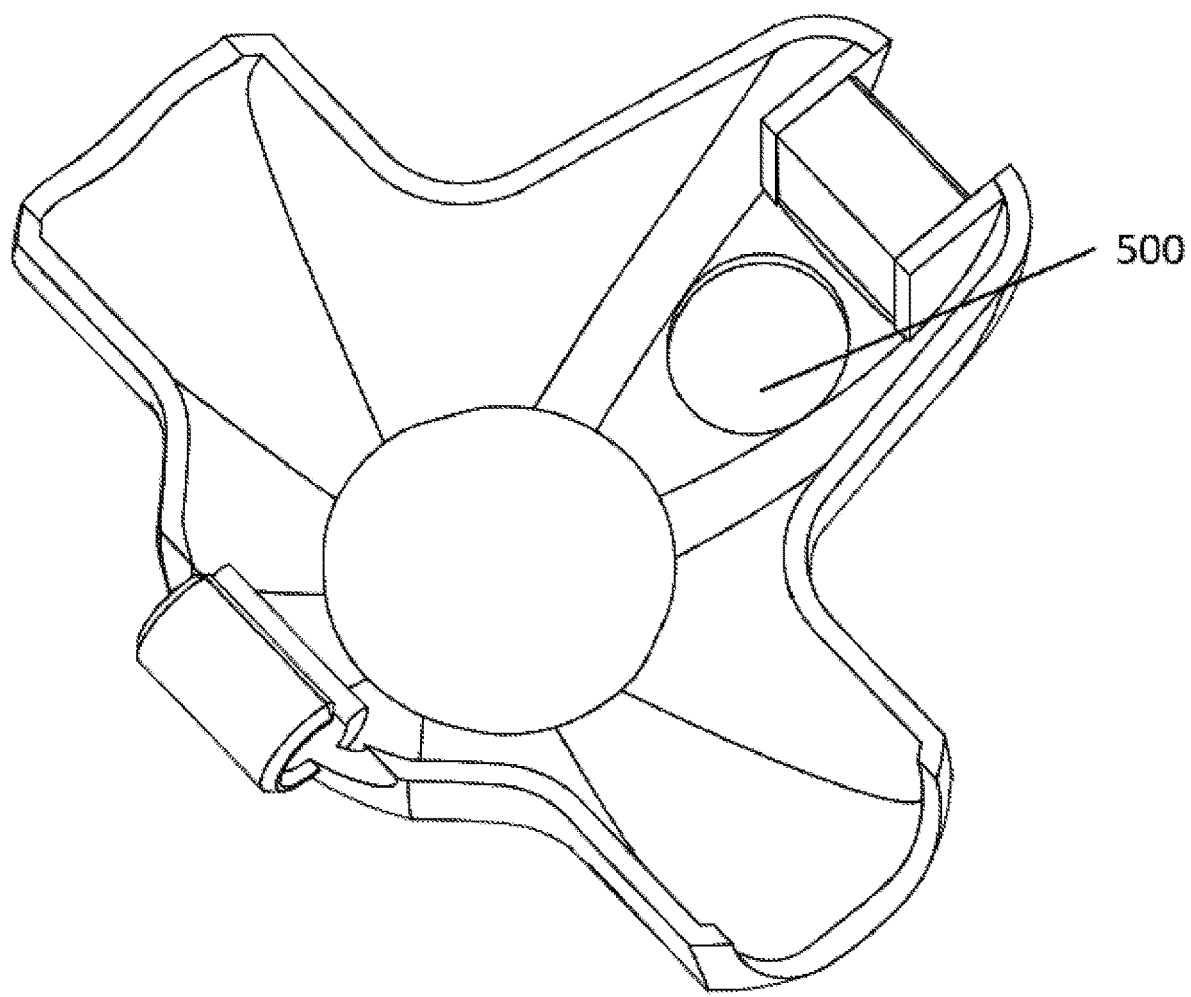
FIG. 9 is an example of a housing embodiment incorporating a light transmitting region or window.
Figure 10:
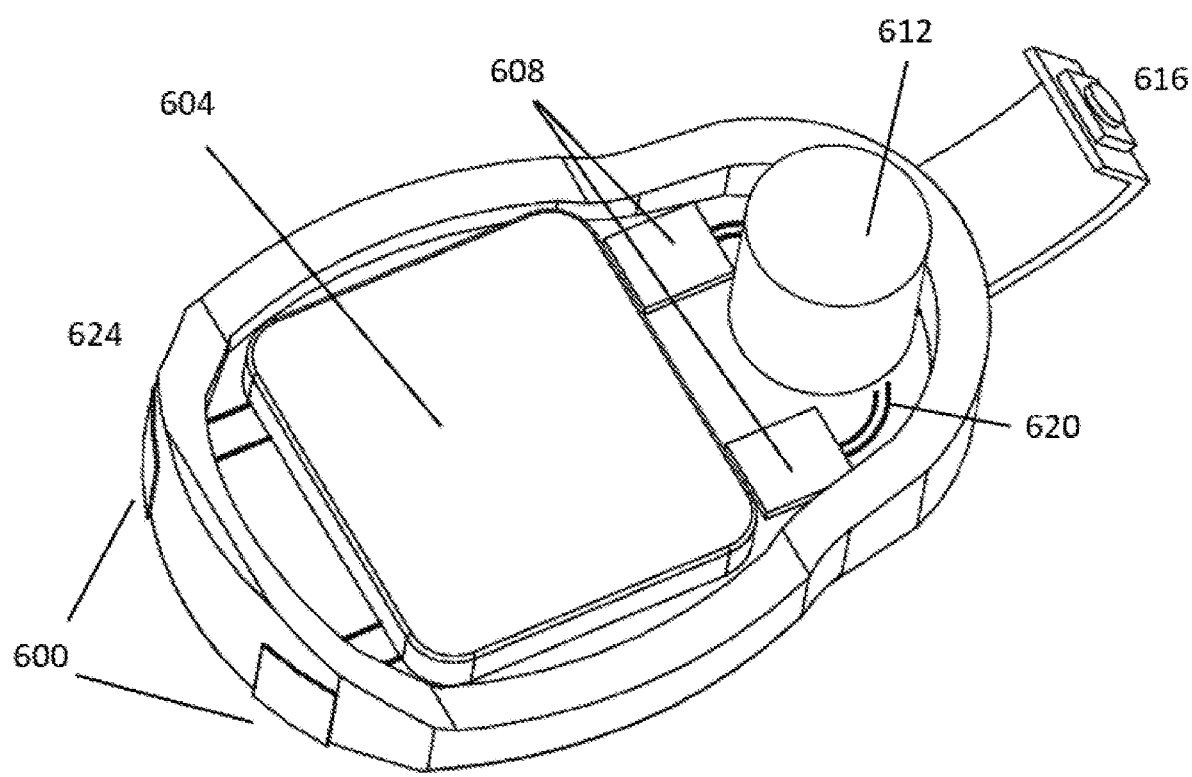
FIG. 10 is an example of a light source configured for use with a device as described herein.
Figure 11:
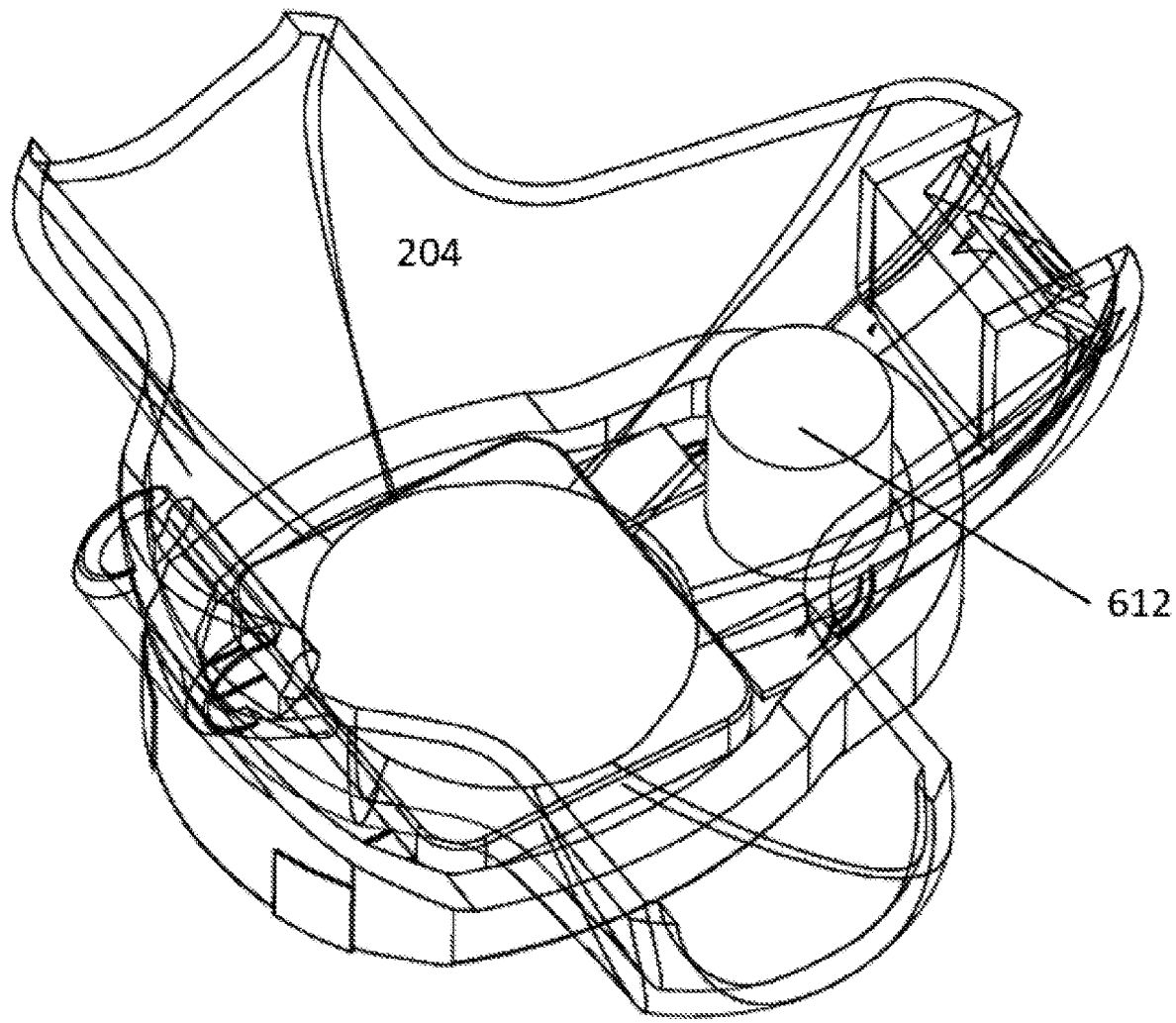
FIG. 11 is an example of a light source integrated into or coupled to a housing.

Referring to FIGS. 9-11, in another aspect a light transmitting region 500 may be disposed on the first housing body 204 and/or the second housing body 208. The light transmitting region 500 may cooperate with an external light source 612 (e.g. ultraviolet light, pulsed xenon, mercury lamp) that may include recharging connections 600, a power source 604, a circuit 608, an activation switch 616, and wires 620, all disposed within a shell casing 624 that can be coupled to the first housing body 204 and/or the second housing body 208.

Figure 12:
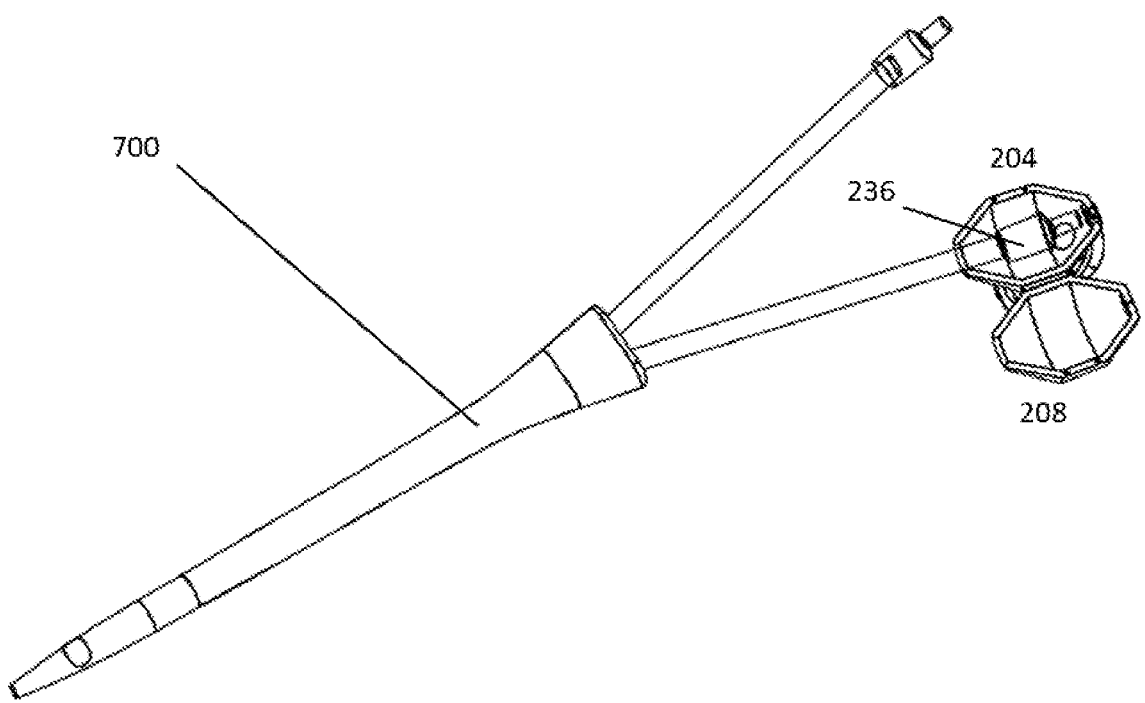
FIG. 12 is an example of a representative housing in use with a catheter port.
Figure 13:
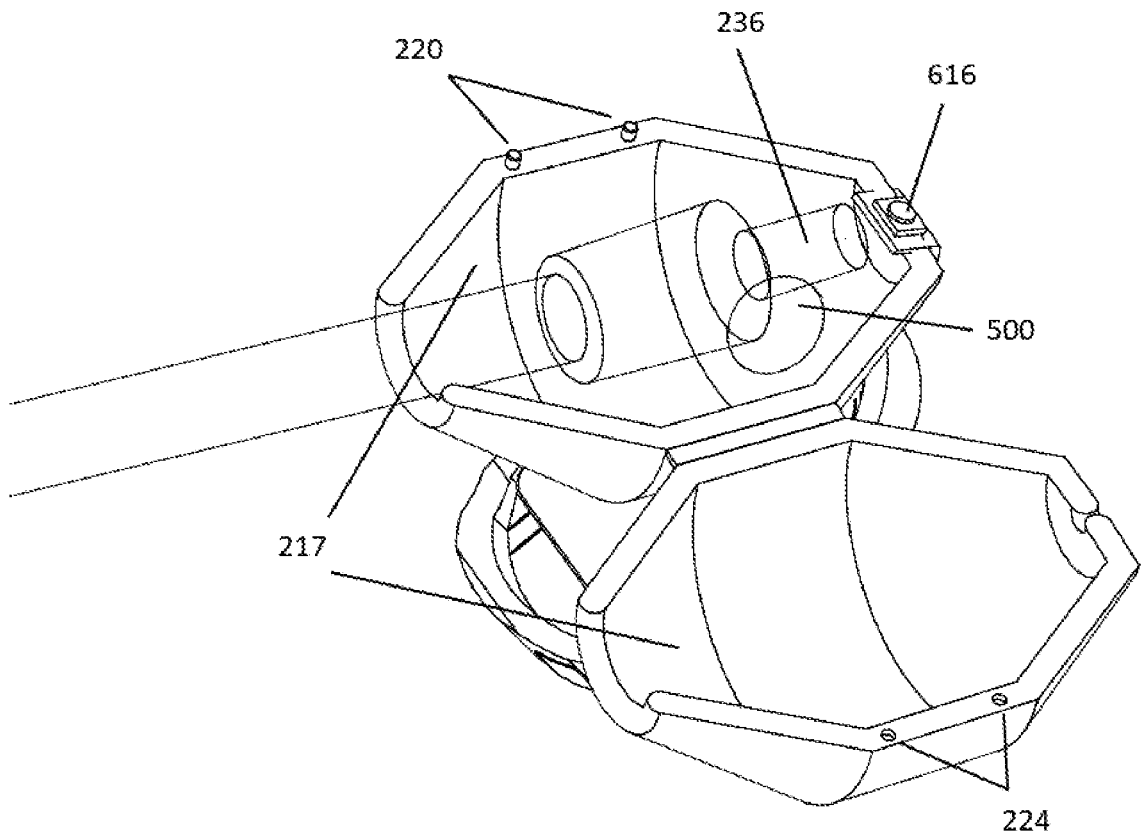
FIG. 13 is a more detailed view of FIG. 12.

Referring to FIGS. 12-13, in another implementation, cap 236 of housing assembly 200 may be coupled to an external percutaneous connection such as an indwelling catheter 700.

The device can have an electronic control unit, memory, and an interactive monitoring module. In certain aspects the device can transmit and receive information to and/or from an outside third party or an in-house data center. A system can include a wired or wireless secondary device such as a mobile phone, a portable tablet, a laptop computer, a desktop computer, and the like that can be included in the system, the device having a connected modality that can send and/or receive information using a wireless connection (e.g., a Bluetooth connection) or a wired connection (e.g., mini USB), etc. The device can have an electronic control unit, memory, and an interactive monitoring module. The monitoring module can be connected physically or wirelessly and can be configured for taking/measuring or accepting data.

Figure 1A:
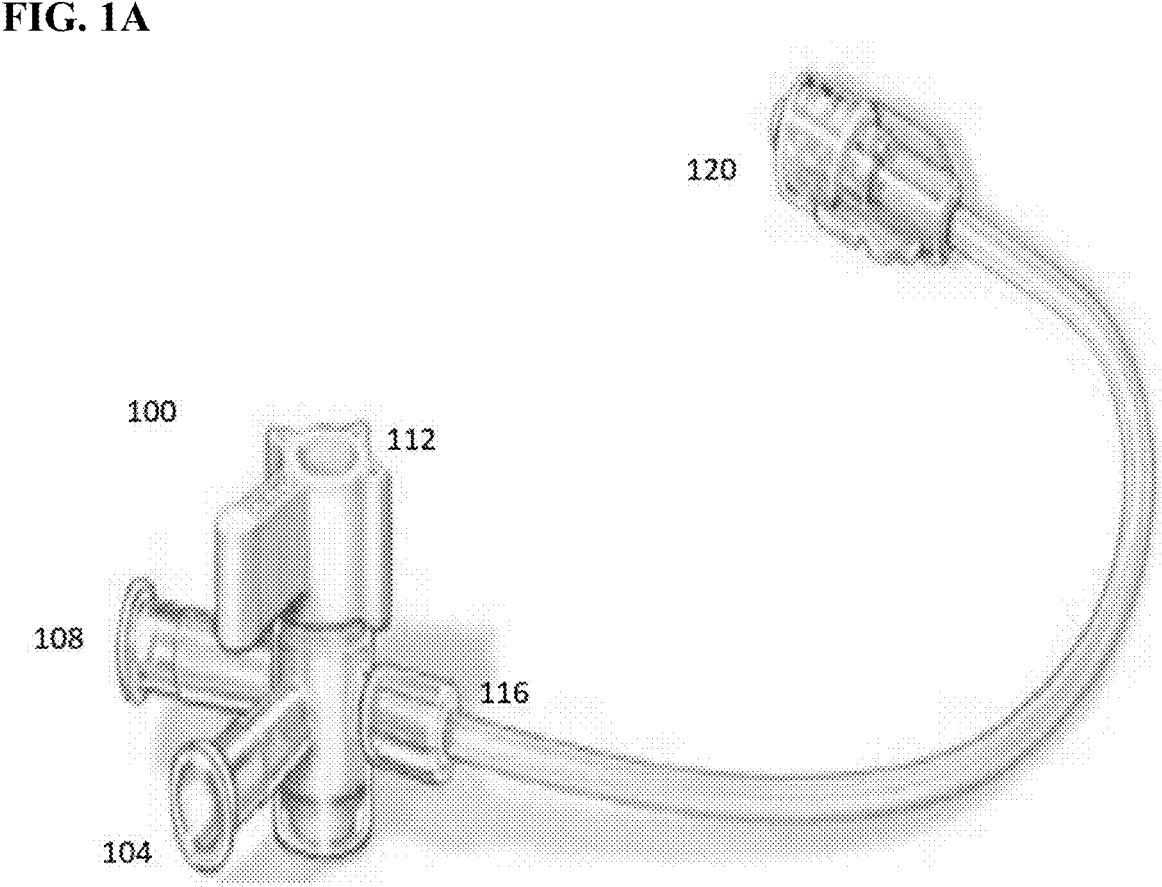
FIGS. 1A-B is a photograph of a three-way stopcock (FIG. 1A) alone, or (FIG. 1B) in use with a syringe.
Figure 1B:
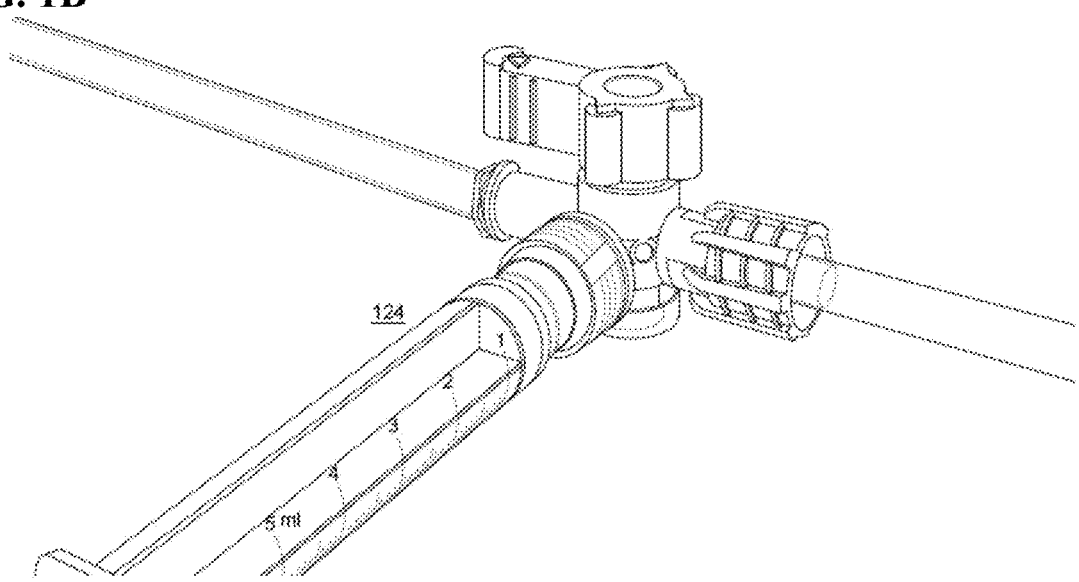
Figure 14A:
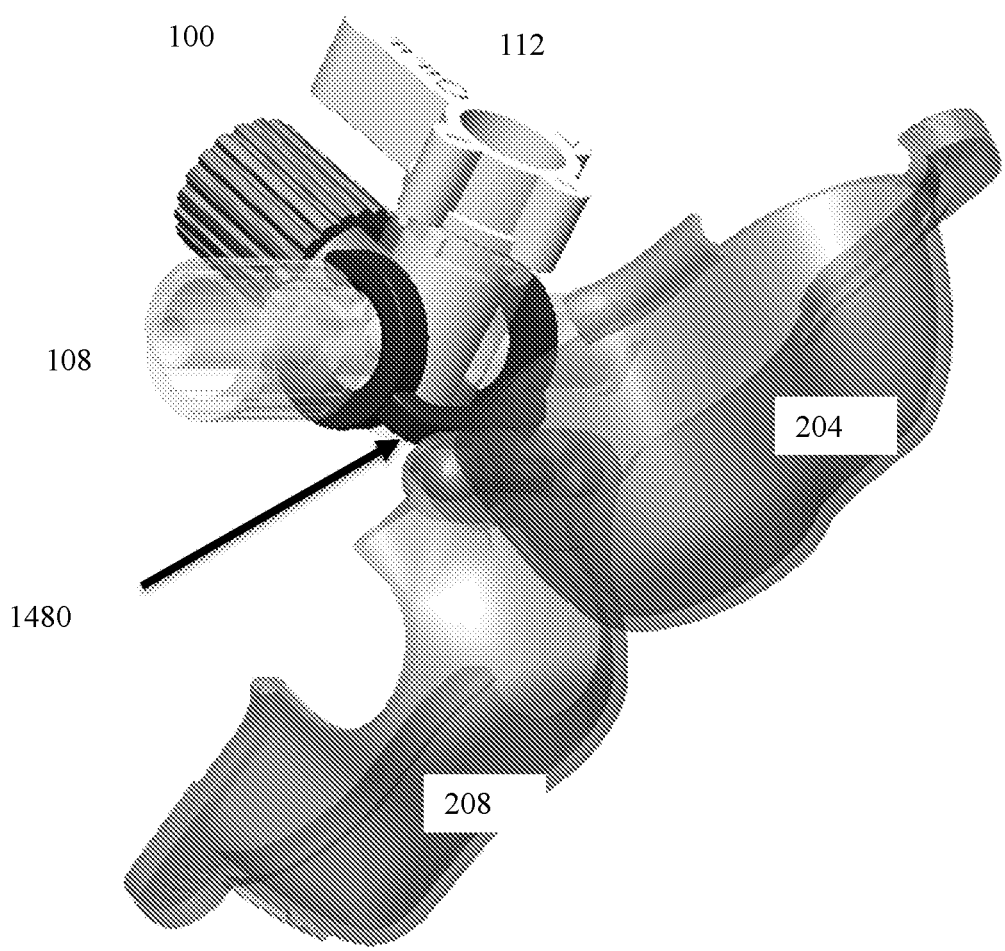
FIGS. 14A and 14B. Illustration of a device incorporating a link connector to provide a connection between the three way and the device. (A) Illustrates the connector coupling a device and a three-way stopcock. (B) Illustrates one embodiment of the link connector in isolation having C shaped connectors configured to clip onto the three-way stopcock and a clip mechanism to secure the link connector to the cover device.
Figure 14B:
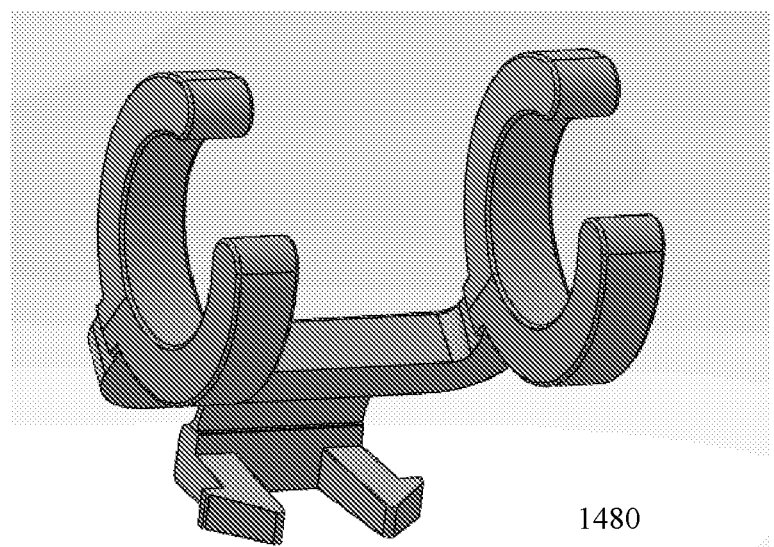
Figure 15A:
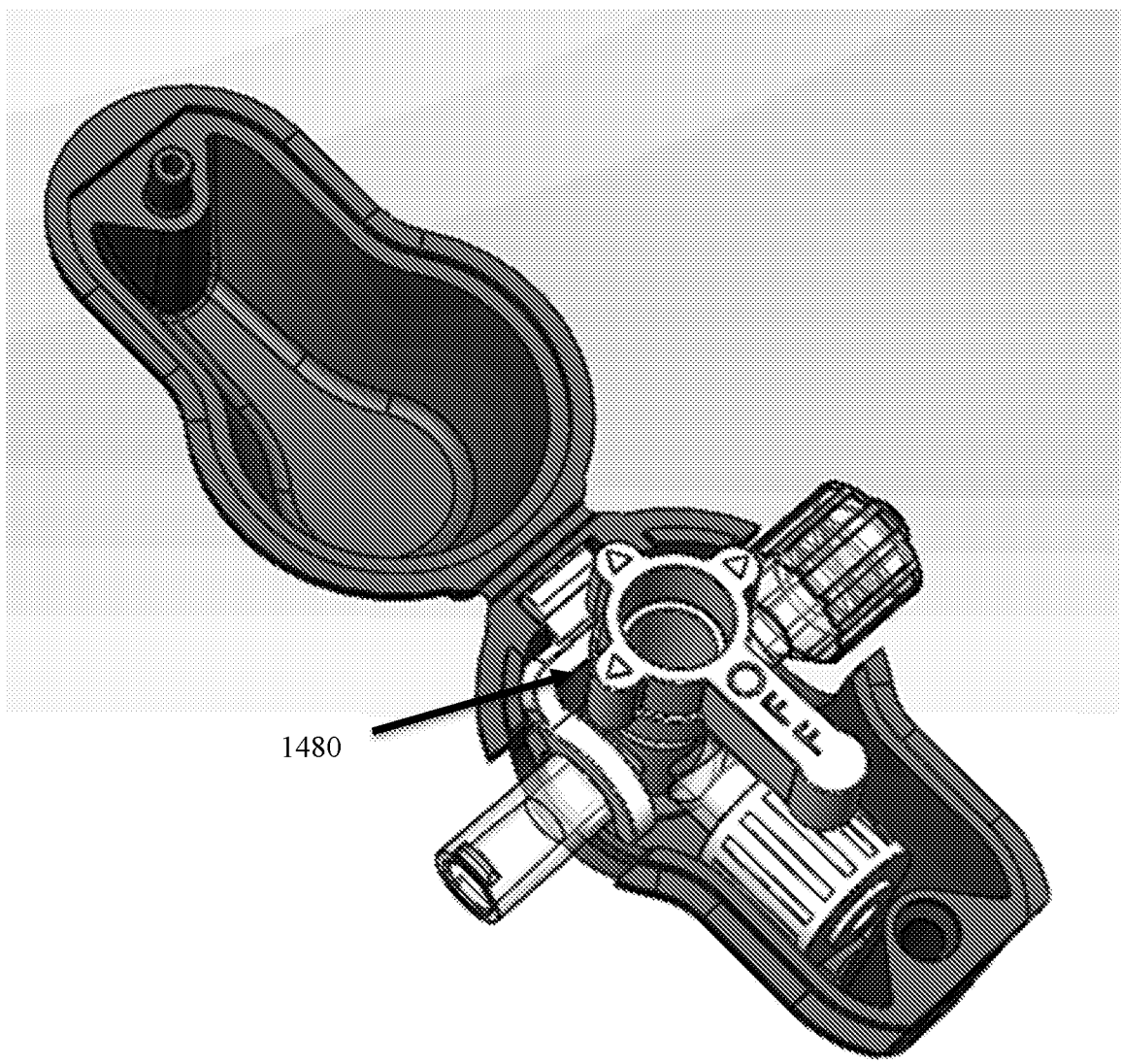
FIGS. 15A and 15B. Illustrates an embodiment in which the three-way stopcock is integrated into the cover device itself (A) Illustration of an open integrated device. (B) a closed integrated device.
Figure 15B:
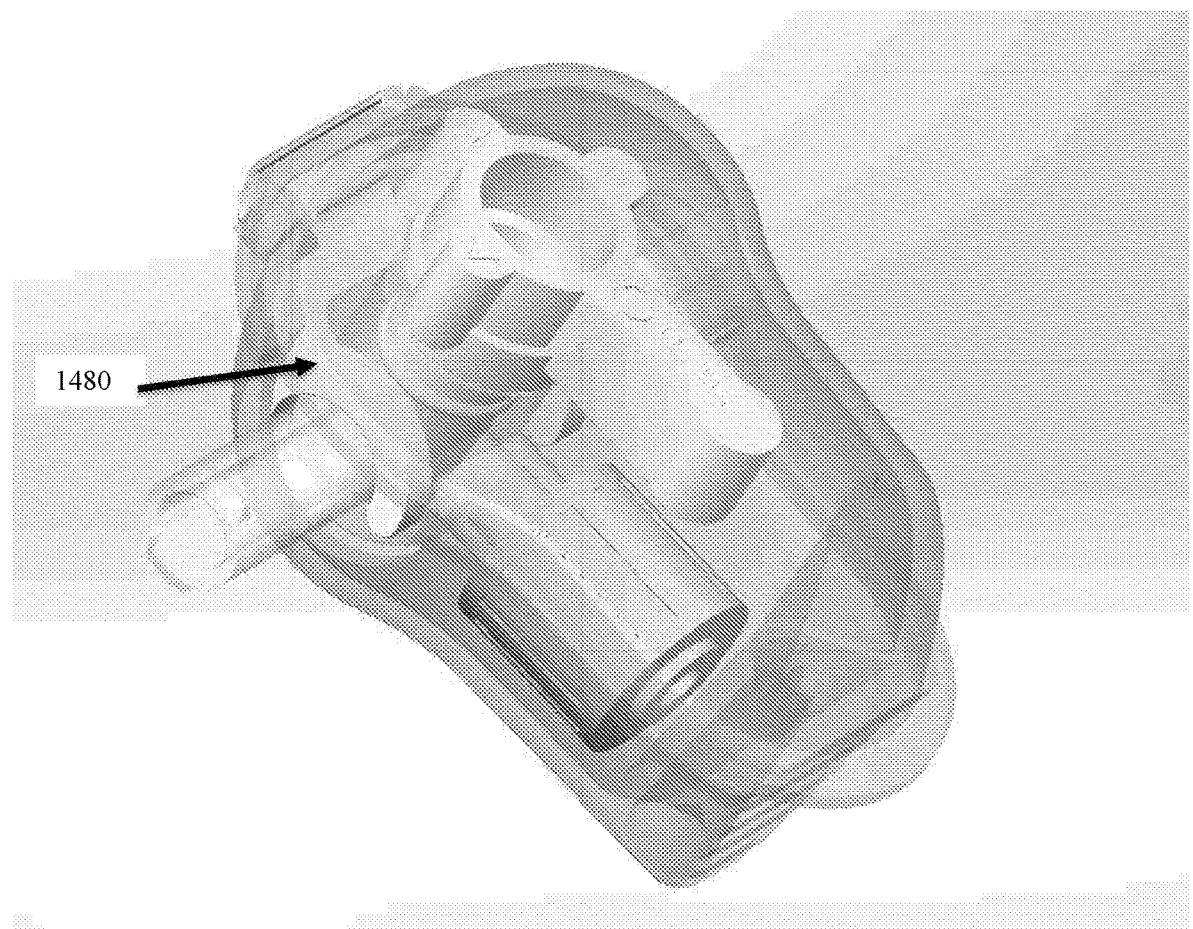

FIG. 14A-14B shows an aspect where the two halves of the cover or housing assembly (see FIG. 2-FIG. 11 for example) are attached to the three-way stopcock (see FIG. 1 and FIG. 2 for an example) through a link connector 1480. The link provides a connection between the back or posterior aspect of the three way and the cover. The link part hinges in the attachment of the shell to give freedom to move the three way when medication administrations are necessary. FIG. 15A-15B illustrates an alternate configuration where link connector 1480 is integrated or built in to the cover or housing assembly (see FIG. 2-FIG. 11 for example).

In certain aspects, a non-disposable UV-light generator can be attached to the front or base of the three-way stopcock, it can have a shape of a console disk, or hand-held scanner. The Hand-held device can provide UV treatment without physically touching the three way. In additional, the hand held deceive can have an infrared (IR) scanner for bar code or optical mark reading, which can provide a certain specific code to activate the UV treatment.

During the process of medication administration during the night, finding the identification arm band is necessary before medication administration. The identification band can incorporate micro-electronic components similar to those described for the line guard device (photosensor, PCB, battery and LED).

II. Method Embodiment

Referring to FIG. 1A, FIG. 1B, FIG. 2, and FIG. 3, the operation of the housing assembly 200 will be described with regard to a three-way stopcock 100 as an illustrative example of a percutaneous connection that may be enclosed and sanitized within the housing assembly 200. Side port female luer 104, outlet port female luer 108, three-way knob 112, inlet line 116, and inlet male luer 120, are oriented by the user to fit on top of the first housing body inner surface 212 or second housing body inner surface 216. Side port female luer 104 may then be connected to the cap 236, which may be configured to be a male luer. The first housing body 204 is then rotated relative to the second housing body 208 from the open position 248 to the closed position 312 so that the three-way stopcock 100 is completely enclosed within the interior chamber 308 of the housing assembly 200. Mateable latch 239 is then engaged to secure the three-way stopcock 100 within the interior chamber. Light source 232 is then activated to sterilize the percutaneous connection. In certain aspects the light source is activated upon closing the housing. In a particular aspect the light source is activated manually. In a particular implementation, locking mechanism male end 220 and locking mechanism female end 224 engage each other when housing assembly 200 is in the closed position 312 to prevent three-way knob 112 from turning inside the interior chamber 308.

The above specification and examples provide a complete description of the structure and use of illustrative embodiments. Although certain embodiments have been described above with a certain degree of particularity, or with reference to one or more individual embodiments, those skilled in the art could make numerous alterations to the disclosed embodiments without departing from the scope of this invention. As such, the various illustrative embodiments of the methods and systems are not intended to be limited to the particular forms disclosed. Rather, they include all modifications and alternatives falling within the scope of the claims, and embodiments other than the one shown may include some or all of the features of the depicted embodiment. For example, elements may be omitted or combined as a unitary structure, and/or connections may be substituted. Further, where appropriate, aspects of any of the examples described above may be combined with aspects of any of the other examples described to form further examples having comparable or different properties and/or functions, and addressing the same or different problems. Similarly, it will be understood that the benefits and advantages described above may relate to one embodiment or may relate to several embodiments.

The claims are not intended to include, and should not be interpreted to include, means-plus- or step-plus-function limitations, unless such a limitation is explicitly recited in a given claim using the phrase(s) "means for" or "step for," respectively.

The invention claimed is:

1. A housing assembly comprising:
a first housing body;
a second housing body pivotally coupled to the first housing body by a hinge, first and second housing body being moveable relative to each other between an open and closed position, wherein the housing assembly forms an interior chamber with one or more openings when in the closed position;
a cap integrated with the hinge and configured to be disposed within the interior chamber and receive a complementary connection.

2. The housing assembly of claim 1, wherein the housing assembly is configured to be reversibly fixed in the closed position.

3. The housing assembly of claim 1, wherein the interior chamber has a reflective surface.

4. The housing assembly of claim 1, further comprising (a) a lip region on the first housing body; and (b) a lip-receiving region on the second housing body forming a reversible latch.

5. The housing assembly of claim 1, wherein the first housing body and second housing body have a smooth outer surface.

6. The housing assembly of claim 1, having a light transmittable region in the first housing body or second housing body, or the first housing body and the second housing body.

7. A housing assembly comprising:
a first housing body;
a second housing body pivotally coupled to the first housing body by a hinge portion, first and second housing body being moveable relative to each other between an open and closed position, wherein the housing assembly forms an interior chamber with one or more openings when in the closed position;
a cap configured to be disposed within the interior chamber and configured to receive a complementary connection, wherein the cap is integrally formed with the hinge portion.

8. The housing assembly of claim 1, wherein the cap and/or the housing assembly is operatively coupled to one or more light source.

9. The housing assembly of claim 8 wherein the light source is an ultraviolet light source.

10. The housing assembly of claim 9, wherein the ultraviolet light source is contained inside the chamber.

11. The housing assembly of claim 9, wherein the ultraviolet light source is activated when the housing is closed.

12. The housing assembly of claim 1, wherein the cap is made of borosilicate glass.

13. The housing assembly of claim 1, wherein the cap is made of a light transmittable polymer.

14. The housing assembly of claim 1, where the housing assembly is configured to be sterilized by a light source external to the first housing body and/or second housing body.

15. The housing assembly of claim 14, where the external light source is a pulsed xenon, LED, mercury lamp, or other source of UV-C radiation.

16. The housing assembly of claim 1, further comprising a detachable multifunction unit.

17. The housing assembly of claim 16, wherein the multifunction unit is configured to provide for one or more of event-time registration, memory storage, timer activation, light color coding, optic sensor for detection of biofilm, finger printer reader, mini-camera and/or mini-speaker.

18. A method comprising:
   connecting a cap of an open housing assembly of claim 1 to a port of a medical device;
   rotating the first housing body relative to the second housing body from the open position to the closed position forming an interior chamber and
   enclosing the cap/port connection within the interior chamber; and
   optionally activating a light source to sanitize the port.

19. The housing assembly of claim 8 wherein the light source is a visible light source illuminating the assembly.

20. The housing assembly of claim 19, wherein the visible light source can provide a color coding to provide information regarding the port attached to the housing assembly.

* * * * *